United States Patent [19]

Lagesson et al.

[11] Patent Number: 4,668,091
[45] Date of Patent: May 26, 1987

[54] ARRANGEMENT AT A GAS FLOW THROUGH CELL FOR SPECTROPHOTOMETRIC ANALYSIS OF CHEMICAL COMPOUNDS

[76] Inventors: Verner Lagesson; Ludmila Lagesson-Andrasko, both of Kobergsgränd 2, S-582 44 Linköping, Sweden

[21] Appl. No.: 690,500
[22] PCT Filed: Apr. 26, 1984
[86] PCT No.: PCT/SE84/00156
§ 371 Date: Dec. 18, 1984
§ 102(e) Date: Dec. 18, 1984
[87] PCT Pub. No.: WO84/04392
PCT Pub. Date: Nov. 8, 1984

[30] Foreign Application Priority Data

May 2, 1983 [SE] Sweden ............................ 8302468

[51] Int. Cl.$^4$ .......................................... G01N 1/10
[52] U.S. Cl. ................................. 356/246; 73/23.1
[58] Field of Search ................... 356/244, 246, 312; 73/23.1

[56] References Cited

U.S. PATENT DOCUMENTS 3,778,156  12/1973  Schmedes et al. ................. 356/244
3,919,279   6/1974  Braun et al. ....................... 356/244

FOREIGN PATENT DOCUMENTS 3132926  1/1982  Fed. Rep. of Germany ...... 356/244
0087843  7/1981  Japan ................................. 356/244

OTHER PUBLICATIONS

"Vergleich von Atomabsorption und Atomfluoreszenz in der Graphitkuvette", H. Massman, Spectrochimica Acta, 1968, vol. 23B, pp. 215–226, Pergamon Press, Northern Ireland.
"The Potentialities of the Graphite Crucible Method in Atomic Absorption Spectroscopy", B. L. L'vov, Spec-trochimica Acta, vol. 24B, pp. 53–70, Pergamon Press 1969, Northern Ireland.
"The Analytical Use of Atomic Absorption Spectra", B. V. L'Vov, Spectrochimica Acta, 1961, vol. 17, pp. 761–770, Pergamon Press Ltd., Northern Ireland.
"Analysis by Means of Atomic-Absorption Spectroscopy, Using a Tantalum Boat", H. V. Lagesson, The Lund Institute of Technology, Chemical Center, Box 740, Lund 7, Sweden, pp. 527–538.
"Present State and the Main Problems of Atomic Absorption Analysis—A Review", B. V. L'Vov, State Institute of Applied Chemistry, Leningrad, translated from Zhurnal Analiticheskoi Khimil, vol. 26, No. 3, pp. 590–608, Mar. 1971 (1971 Consultants Bureau, Division of Plenum Publishing Corporation, New York, New York, pp. 510–529).

Primary Examiner—Vincent P. McGraw
Assistant Examiner—S. A. Turner
Attorney, Agent, or Firm—Hayes, Davis & Soloway

[57] ABSTRACT

The present invention relates to a gas flow cell for spectrophotometric analysis of chemical compounds, consisting of a longish preferably cylindrical body (1) with a longitudinal central channel (2) which at the ends of the body (1) is limited by mutually parallel windows (3, 4) which are tightfitting against the channel (2) and transparent for the radiation used at the analysis. The channel (2) communicates at one end with connections (7, 8) for carrier gas and for injection of compounds and has at the other end an outlet (10) for the compounds and the carrier gas. Significant for the invention is that parallel with and at a distance from the mentioned channel (2) runs a second channel (11) serving for separation and connected between the connections (7, 8) and said end of the first mentioned channel (2). In this channel (11) there is a replaceable column tube (12) with filling of known composition.

2 Claims, 4 Drawing Figures

ARRANGEMENT AT A GAS FLOW THROUGH CELL FOR SPECTROPHOTOMETRIC ANALYSIS OF CHEMICAL COMPOUNDS

The present invention relates to an arrangement at a gas flow cell for spectrophotometric analysis of chemical compounds in the gas phase consisting of a longitudinal preferably cylindrical body with a longitudinal central channel which at both ends of the body is limited by two mutually parallel windows which are tighfitting against the channel and transparent for the radiation used at the analysis, which channel communicates at one end with connections for a carrier gas and for injecting compounds and at the other end has an outlet for the compounds and the carrier gas.

BACKGROUND OF THE INVENTION

That part of analytical chemistry which is dealing with separation and detection of organic compounds in mixtures has ever since in the sixties been dominated by gas chromatography where the detection normally is obtained by an unspecific detector. More recently the technique has developed towards combinations of gas chromatography (GC) with qualitative analytical methods like mass spectroscopy (MS), IR-spectrophotometry (IR) or UV-spectrophotometry (UV). The advantage with these combinations is first of all that it gives possibilities for identification of compounds which are separated on the gas chromatograph. Further on it gives the possibility to achieve selective detection for example by selecting a wavelength on the UV- or IR-detector where only aromato compounds gives a response.

DRAWBACKS OF KNOWN TECHNIQUE

Gas chromatographs has in general a size and complexity which imply that the instrument must be permanently installed in one place. The injector, column and detector are further on individually heated and the possibilities for identification of an unknown compound is strongly restricted with conventionel instruments equipped with unspecific detectors. Additional drawbacks are lengthy start up times, occasionally relatively long analysis times and high instrument costs.

Commersially available instrument combinations exist for GC/IR and for GC/MS but not for GC/UV. The commercial combination of instruments are very costly and have complicated connections between the gas chromatograph and the spectrophotometer which makes it considerably difficult for changing to other analytical techiques like IR-analysis of compounds in the liquid phase. The high costs and the complexity has led to that most analytical laboratories with a particularly quantitative direction will have restricted possibilities for identification of compounds.

OBJECT OF THE INVENTION

A primary object of the invention in question is to achieve a gas flow cell by initially described kind, by which the combinations GC/UV and GC/IR as well as enrichment of compounds can be carried out.

This is obtained according to the primary characteristic of the invention in that there is a second channel serving for separation connected between the connections and one of the ends of the first mentioned channel, in which channel there is replaceable column with column filling of a kind known per se.

In that the body, according to a special characteristic of the invention, is of an electrically leading polymeric material of a temperature self-regulating quality and has electric connections so that the body can be heated by connection to a voltage supply is obtained that through utilization of the body as a resistor element with temperature self-regulating characteristic depending on increasing resistance with increasing temperature the cell can be heated in a way that a good separation of the compounds is achieved.

SHORT DESCRIPTION OF THE DRAWING

In the following the invention will be further explained with reference to the attached drawing on which FIG. 1 in perspective shows a gas flow cell according to the present invention.

DESCRIPTION OF AN EMBODIMENT

Figure 1:
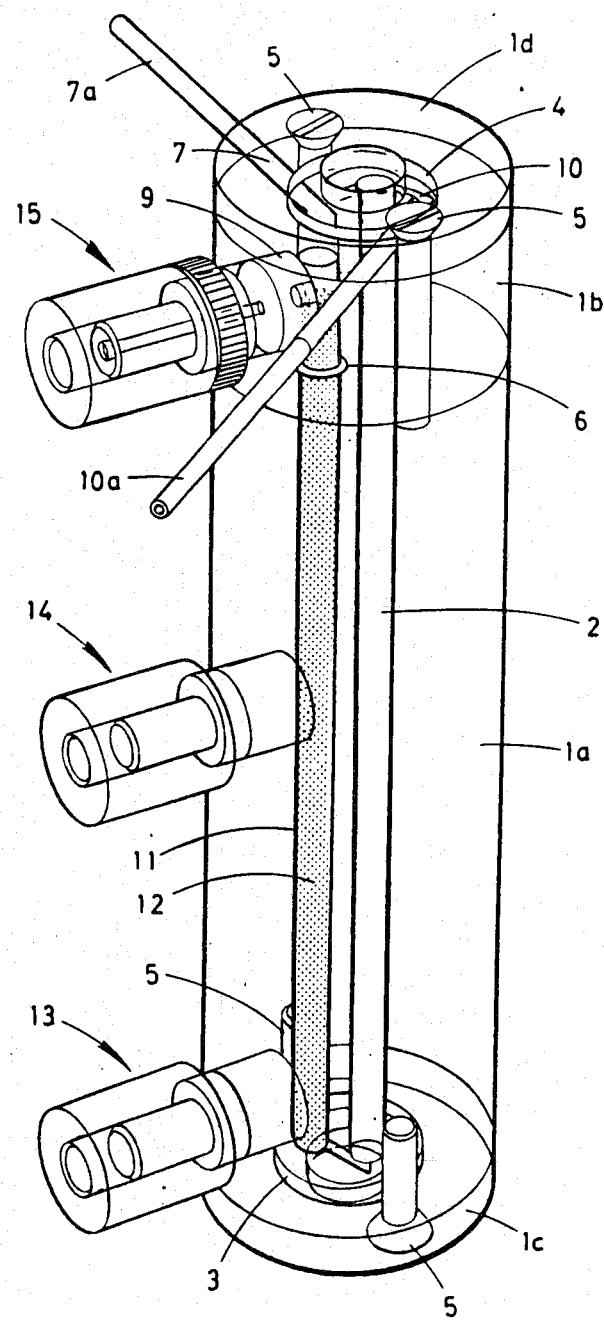

On the drawing numeral 1 represents a longish preferably cylindrical body with a longitudinal central channel 2. The body 1 preferably has such dimensions that if fits in the cuvette housing of a spectrophotometer and owing to technical and constructive reasons is made in four parts 1a, 1b, 1c and 1d which are kept together by screws 5 and, where so is necessary, are sealed with O-rings 6. Channel 2 is restricted at the both ends of the body 1 by mutually parallel windows 3,4 which are kept in place by the parts 1c and 1d and which are tightly connected to the channel 2. The windows 3, 4 are transparent for the radiation used at the analysis e.g. quartsglass at UV-detection and at IR-detection an IR-transparent material for example ZnSe. Channel 2 communicates partly with a connection channel 7 for carrier gas and partly with a connection channel 8 for injection the mixtures of compounds which are going to be analysed. In the connection channel 8 there is a sealing injection membrane 9 through which injection can be carried out by a syringe. The opposite end of the channel 1 commuincates with an outlet channel 10 for the compounds and the carrier gas. On the outside of the body there are connection tubes 7a and 10a which communicate with channels 7 and 10 respectively.

Figure 2:
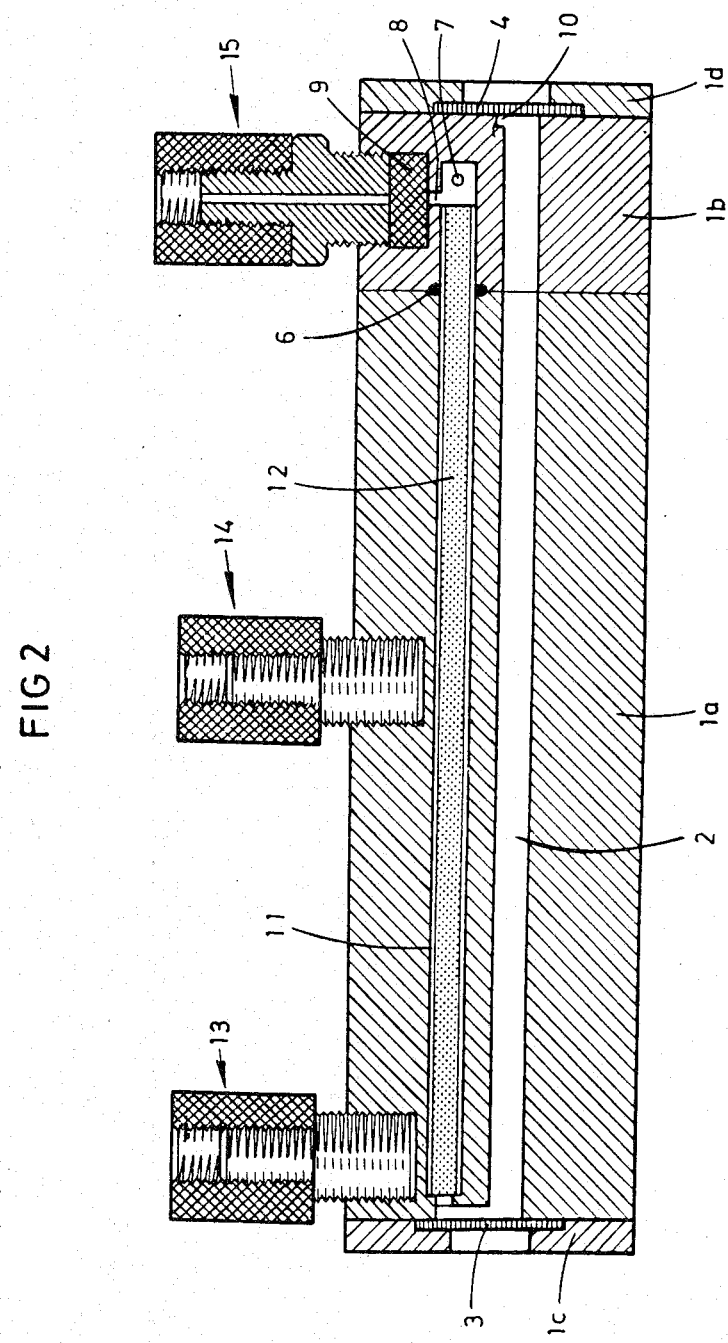
FIG. 2 shows a longitudinal section through the gas flow cell in FIG. 1.
Figure 3:
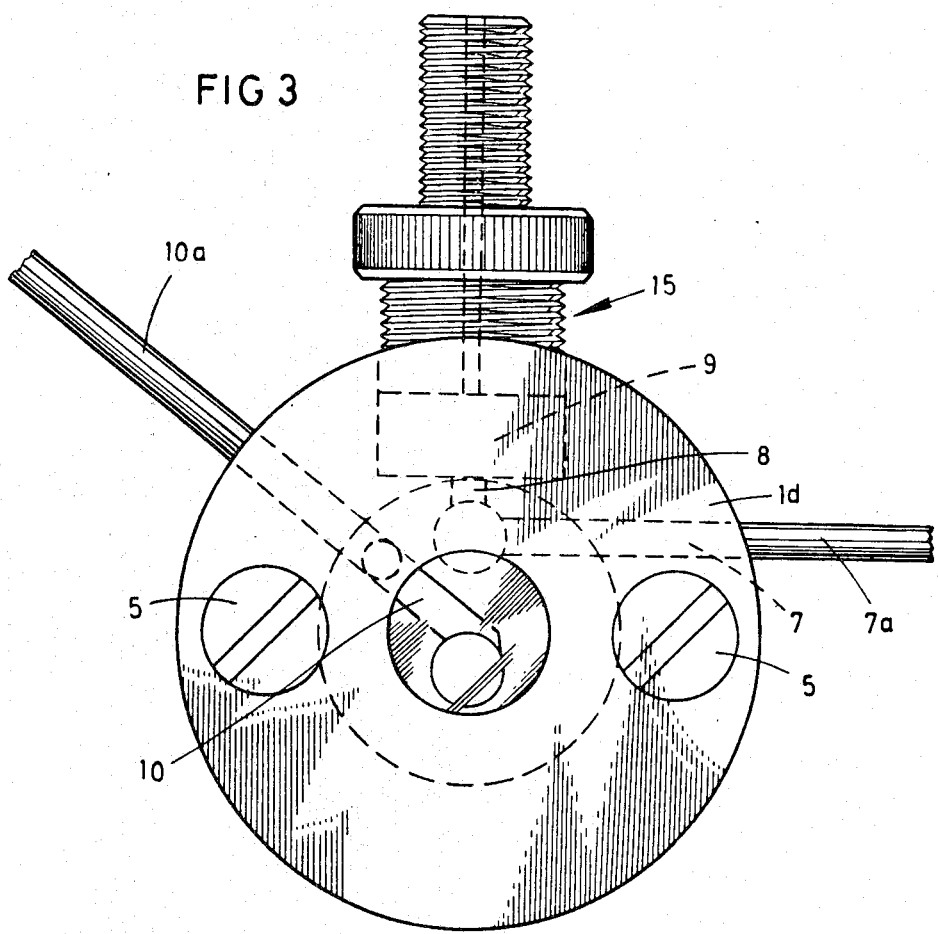
FIG. 3 and 4 show one of the ends of the gas flow cell seen in axial direction respectively across this direction.
Figure 4:
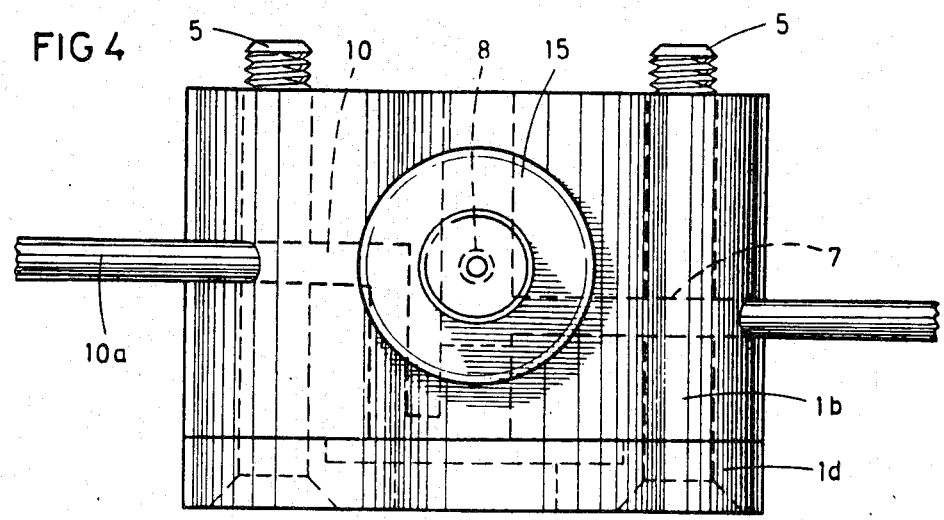

According to the invention there is a channel 11 serving for separation and/or enrichment connected between the connections 7,8 in which there are a replaceable column tube with a composition known to a man skilled in the art. Channel 2 and 11 communicate with each other at the both ends turned against the window 3 at the left hand side in FIG. 2. The channel 11 with the column tube 12 and its filling serves for separation of different compounds in a sample as will be explained in the following.

As is known there is as a rule a requirement for a defined temperature increase in order to separate different compounds in a sample. According to the present invention for this reason the body is therefore made of an electrically conducting material e.g. a carbon filled polymeric with self-regulating temperature characteristic and equipped with connections 13, 14, 15 which can be connected to controlled voltage supply either by parallel connection through 13 and 14 resp 14 and 15 or in a series connection i.e. through 13 and 15 so that different kinds of heating of the body can be carried out.

The channel 8 for the injection of the sample which is analysed goes through the connection 15.

As can be seen the column tube 12 of the instrument is extremely short. In order to obtain comparable separation capacity as for conventionally packed GC-columns the support material in the column tube 12 is of considerably smaller particle sizes. These support materials are commercially available as column filling materials for liquid chromatography. The liquid phase can be applied in a manner similar to what is usual for normal GC-supports.

DESCRIPTION OF AN ANALYSIS EXAMPLE

The gas flow cell is placed in a spectrophotometer and the connection tube 7a for the carrier gas is connected to a gas supply and the electrical connections 13-15 to a voltage supply, not shown in the drawing. By applying a defined voltage over the poles 13-15, a defined temperature is achieved in the body 1. The sample is injected through the injection membrane 9 and is forced out in the space just in front of the separation column 12. Injection of samples can be carried out either in the gas phase or in the liquid phase. The compound in the sample is separated in a known way in the liquid phase. The compound in the sample is separated in a known way in the column. When the separated compounds reach the channel 2, they are registered by the spectrophotometer and the absorbance (proportional against concentration) and signal from the detector of the spectrophotometer can be recorded on a recorder or treated by an integrator in an usual manner.

Selective detection of compound groups are obtained by the selection of a suitable wavelength on the spectrophotometer.

At identification of compounds the analysis procedure is somewhat depending on the characteristics of the spectrophotometer. Advanced spectrophotometers having fast scanning possibilities can deliver a complete wavelength spectra while the compound is passing through the gas flow cell. When simpler and slower spectrophotometers are used the gas flow is stopped when the compound is in position in the gas cell and the spectra is registered from the captured compound whereupon the gas flow again is allowed to flow.

We claim:

1. Arrangement at a gas flow cell for spectrophotometric analysis of chemical compounds in the gas phase comprising a longish preferably cylindrical body having a first longitudinal channel which at each end of the body is closed mutually parallel windows which are tight fitting and are transparent for the radiation used at the analysis, said body communicating at one end with connections for a carrier gas and for injecting compounds and at the other end has an outlet for the compounds and the carrier gas, characterised in that, there is a second channel serving for separation and/or enrichment connected between the injection connection and one end of the first longitudinal channel, said second channel containing a replaceable column tube with column filling for chromatographically separating gaseous components of said injected compounds.

2. Arrangement according to claim 1 characterized in that, the body is made of an electrically conducting material preferably a polymeric material which has a temperature self-regulating characteristic by increasing resistance at increasing temperature.

* * * * *